United States Patent
Prockop et al.

(10) Patent No.: US 7,056,738 B2
(45) Date of Patent: Jun. 6, 2006

(54) EARLY STAGE MULTIPOTENTIAL STEM CELLS IN COLONIES OF BONE MARROW STROMAL CELLS

(75) Inventors: Darwin J. Prockop, New Orleans, LA (US); David C. Colter, Philadelphia, PA (US); Ichiro Sekiya, New Orleans, LA (US)

(73) Assignees: Tulane University, New Orleans, LA (US); Philadelphia Heath and Education Corporation, Philadelphia, PA (US)

( * ) Notice: Subject to any disclaimer, the term of this patent is extended or adjusted under 35 U.S.C. 154(b) by 339 days.

(21) Appl. No.: 09/816,182

(22) Filed: Mar. 23, 2001

(65) Prior Publication Data

US 2002/0168765 A1    Nov. 14, 2002

(51) Int. Cl.
*C12N 5/08* (2006.01)
*C12N 5/00* (2006.01)
*C12N 5/02* (2006.01)

(52) U.S. Cl. .................. 435/372; 435/325; 435/366

(58) Field of Classification Search .............. 435/325, 435/366, 372, 377, 353, 354
See application file for complete search history.

(56) References Cited

OTHER PUBLICATIONS

Deans et al. (2000) Mesenchymal stem cells: Biology and potential clinical uses. Exp. Hematology 28: 875-884.*
Azizi et al. 1998, Proc. Natl. Acad. Sci USA 95:3908-3913.
Beresford et al. 1992, J. Cell Sci. 102:341-351.
Bruder et al. 1997, J. Cell Biochem 64:278-294.
Caplan et al. 1991, J. Orthoped 9:641-650.
Castro-Malaspina et al. 1981, Blood, 56:289-301.
Chopp et al. 2000, Neuroreport II:3001-3005.
Colter et al. 2000, Proc. Natl. Acad. Sci 97:3213-3218.
DiGirolamo et al. 1999, Br. J. Haematol 107:275-281.
Ferrari et al. 1998, Science 279:1528-1530.
Friedenstein et al. 1970, Cell Tissue Kinet 3:393-403.
Goodell et al. 1997, Nat. Med. 3:1337-1345.
Gronthos et al. 1999, J. Bone Miner. Res. 14:47-56.
Hou et al. 1999, Proc. Natl. Acad. Sci. 96:7294-7299.
Jackson et al. 1999, Proc. Natl. Acad. Sci 96:14482-14486.
Johnstone et al. 1998, Exp. Cell Res. 238:265-272.
Clark et al. 1995, Ann N.Y. Acad. Sci. 770:70-78.
Kopen et al. 1999, Proc. Natl. Acad. Sci USA, 96:10711-10716.
Kuznetsov et al. 1997, Br. J. Haematol 97:561-570.
Mets et al. 1985, Mech, Ageing Dev. 16:81-89.
Nilsson et al. 1999, J. Exp. Med. 189:729-734.
Pereira et al. 1995, Proc. Natl. Acad. Sci. USA 92:4857-4861.
Piersma et al. 1985, Exp. Hematol 13:237-243.
Pittenger et al. 1999, Science 284:143-147.
Prockop et al. 1997, Science 276:71-74.
Wakitani et al. 1995, Muscle Nerve 18:1417-1426.
Walsh et al. 2000, Bone 27:185-195.
Woodbury et al. 2000, J. Neuroscience Res. 61:364-370.

* cited by examiner

*Primary Examiner*—Anne-Marie Falk
(74) *Attorney, Agent, or Firm*—Drinker Biddle & Reath LLP

(57) ABSTRACT

Marrow stromal cells (MSCS) are adult stem cells from bone marrow that can differentiate into multiple non-hematopoietic cell lineages. Colonies of human MSCs were shown to contain both small, rapidly self-renewing stem cells (RS cells) and large, more mature cells (mMSCs). Samples enriched for RS cells had a greater potential for multipotential differentiation than samples enriched for mMSCs. Also, RS cells have a series of surface epitopes and expressed proteins that can be used to differentiate RS cells from mMSCs. The results suggest that it will be important to distinguish the two major sub-populations of MSCs in defining their biology and their potentials for cell and gene therapy.

9 Claims, 4 Drawing Sheets

EARLY STAGE MULTIPOTENTIAL STEM CELLS IN COLONIES OF BONE MARROW STROMAL CELLS

STATEMENT REGARDING FEDERALLY SUPPORTED RESEARCH OR DEVELOPMENT

This invention was supported in part using U.S. Government funds (National Institutes of Health Grant Nos. AR47161 and AR44210), and the U.S. Government may therefore have certain rights in the invention.

BACKGROUND OF THE INVENTION

Bone marrow contains at least two kinds of stem cells, hematopoietic stem cells and stem cells for non-hematopoietic tissues (1–27) variously referred to as mesenchymal stem cells or marrow stromal cells (MSCs). MSCs are of interest because they are easily isolated from a small aspirate of bone marrow, they readily generate single-cell derived colonies (1, 2, 5, 18, 21, 25, 27), the single-cell derived colonies can be expanded through as many as 50 population doublings in about 10 weeks (25), and they can differentiate into osteoblasts, adipocytes, chondrocytes (1–13), myocytes (9), astrocytes, oligodendrocytes, and neurons (17, 23, 26, 27). For these reasons, the cells are currently being tested for their potential use in cell and gene therapy of a number of human diseases (22, 24).

There is a long felt need in the art for the generation of large numbers of homogeneous cells for use in alleviating disease in and of themselves, or as delivery vehicles for in gene therapy applications. The present invention satisfies these needs.

BRIEF SUMMARY OF THE INVENTION

The invention relates to the identification and characterization of two classes of bone marrow stem cells, small rapidly self-renewing stem cells (RS cells) and large more mature marrow stromal cells. The invention also relates to methods of their use.

BRIEF DESCRIPTION OF THE DRAWINGS

FIGS. 1A and 1B, are images of two phase-contrast photomicrograph of two different colonies of human MSCs 6 days after the cells were plated at 3 cells/cm$^2$. Arrows indicate one large mMSC and three doublets of recently replicated RS cells. Magnification: 200X.

FIGS. 2A–2E, is a series of images of photomicrographs. FIGS. 2A–2C are a series of images of phase-contrast photomicrographs of a dividing RS cell taken at intervals of 20 minutes. FIG. 2D is an image of an electron photomicrograph of two RS cells. FIG. 2E is an image of an electron photomicrograph of an mMSC. RS cells were prepared by lifting 14 day cultures of MSCs and passing the cells through a 10 micron filter (Millipore). FACS assays (25) indicated that about 95% of the cells in the filtrate were RS cells. Cells on the filter were used as a source of mMSCs. FACS assays indicated that about 90% of these cells were mMSCs. These cells were pelleted by centrifugation, fixed in 2% glutaraldehyde and cut into 3 mm$^3$ blocks. The samples were stained with 2% osmium and 2% aqueous uranyl acetate. After dehydration, the blocks were cut into 70 micron sections. The sections were stained with alcoholic uranyl acetate and counter-stained with bismuth subnitrite. Images were obtained with an electron microscope (JOEL JEM 1010) and a CCD camera (Hamamatsu). As indicated here, the mMSCs were vacuolated and frequently binucleate. The bar is 5 microns.

FIGS. 4A–4F, is a series of images depicting the results of assays for cell differentiation. FIG. 4A depicts cell preparations enriched for RS cells incubated in osteogenic medium for 21 days (33). The mineral in the cultures was detected by staining with Alizarin Red. FIG. 4B depicts a cell fraction enriched for mMSCs incubated in osteogenic medium for 21 days. FIG. 4C depicts a cell fraction enriched for RS cells incubated in adipogenic medium for 21 days (33). Fat droplets in the cells were stained with Oil Red O. FIG. 4D depicts a cell fraction enriched for mMSCs incubated in adipogenic medium for 21 days. FIG. 4E depicts a cell fraction for RS cells incubated under chondrogenic conditions for 21 days (33). Proteoglycans in paraffin sections of the pellet were stained with Safranin O. FIG. 4E depicts a cell fraction enriched for MMSCS incubated under chondrogenic conditions for 21 days.

DETAILED DESCRIPTION OF THE INVENTION

Figure 1:
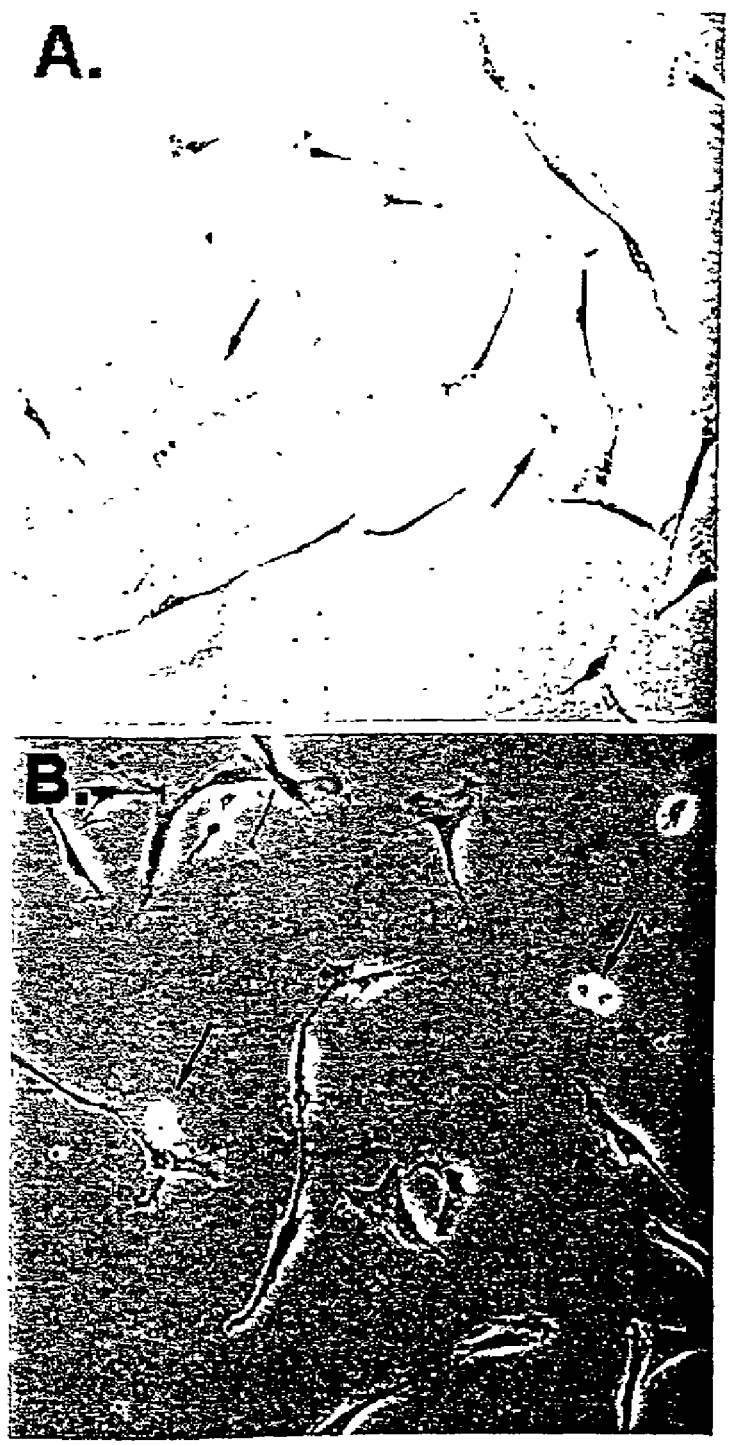
FIG. 1, comprising

The present invention extends the observation that single-cell derived colonies of human MSCs are heterogeneous in that they contain at least two different types of cells: Small and rapidly self-renewing stem cells (RS cells) and large, more mature cells (mMSCs). It is demonstrated herein that RS cells have a greater potential for multilineage differentiation than mMSCs and a series of expressed proteins has been identified that can be used to distinguish the two cell types such that subsets of RS cells can now be identified and therefore can be isolated for use in therapy.

The invention relates to the discovery that a population of small and rapidly self-renewing bone marrow stem cells (RS) may be further subdivided and characterized and differentiated from mMSCs on the basis of the unique expression of selected polypeptides when compared with a population of the more large, more mature marrow stromal stem cells (mMSC). RS cells the cells have been characterized a posteriori based on their varying capacities to differentiate. According to the methods of the present invention, these RS cells and MSCs may be distinguished by their protein expression profiles and a series of surface markers (epitopes) have been discovered which can be used to isolate the earliest progenitor cell of the population of marrow stem cells being studied.

Cells within a population of RS cells express one or more polypeptides selected from the group consisting of VEGF receptor-2(FLK-1), TRK (an NGF receptor), transferrin receptor, and annexin II (lipocortin 2). Cells within the population may also express one or more polypeptides selected from the group consisting of multidrug resistance protein, epithelial membrane antigen, CD4, CD104, CD117, heat shock protein-27, tumor rejection antigen, glutathione-S transferase, peroxiredoxin 1, voltage-dependent-anion channel-2, protein kinase C substrate, phosphatase 2A inhibitor, esterase D, RNase A, initiation factor 5a, elongation factor 1-alpha, ribosomal protein S12, ribosomal protein large P1, ribosomal protein large P2, transcription factor BTF 3a, annexin I, destrin, myosin light chain, lactate dehydrogenase A, glycerolaldehyde-3-P dehydrogenase, citrate synthetase, transketolase, P-glycerolmutase, aldo-keto reductase 7(A2), alpha-amylase inhibitor CM3, enoyl-CoA hydratase, and proteosome subunit alpha-4.

Further in the invention it has been discovered that the RS cells of the invention express at least twenty-nine polypeptides which are not expressed in a population of large, more mature marrow stromal cells (mMSC).

In addition, the invention includes a population of large, more mature marrow stromal cells, mMSC, wherein the cells within the population express one or more polypeptides selected from the group consisting of STRO-1, PDGF receptor, EGF receptor, CD10, and CD147.

In a preferred embodiment, the cells in the MSC population of cells express one or more polypeptides selected from the group consisting of stress protein T-complex protein 1-alpha, initiation factor 2G, ribosomal large P0, annexin V, actin β chain, lactate dehydrogenase B, phosphoglycerate kinase-1, enolase-1, and protein disulfide isomerase ER60 precursor. In addition, these cells express at least nine polypeptides which are not expressed in the population of small rapidly renewing stem (RS) cells.

The invention additionally includes a means for distinguishing a population of small and rapidly self-renewing stem cells (RS) from a population of large, more mature marrow stromal cells (mMSC). It has been discovered that at least about twenty-nine polypeptides are expressed in the population of small and rapidly self-renewing stem cells, but not in the population of large, more mature marrow stromal cells, and further, at least about nine polypeptides are expressed in the population of large, more mature marrow stromal cells, but not in the population of small and rapidly self-renewing stem cells. Thus, the cells are distinguished from each other.

Each of the cells recited herein can be further characterized in that none of the cells express any of the polypeptides selected from the group consisting of CD1a, CD11B (Mac-1), CD14, CD27, CD34, CD43, CD45, CD133, CD50 (I-CAM 3), CD53, CD109, CD114(G-CSFR), HLA-2, CCR5 (chemokine receptor-5) and human L1 (neurite adhesion molecule). Moreover, as the data presented herein establishes, the population of small and rapidly self-renewing stem cells are about 7 microns in diameter and the population of large, more mature marrow stromal cells of about 15-50 microns in diameter.

The invention includes a population of small and rapidly self-renewing stem (RS) cells identified and characterized by the methods disclosed herein, and a population of large, more mature marrow stromal cells )MSCs) identified by the methods disclosed herein.

Methods of isolating marrow stromal cells and their use in cell and gene therapy are disclosed in WO96/30031 and WO99/43286, each of which is hereby incorporated herein by reference.

The invention is now described with reference to the following example. This example is provided for the purpose of illustration only and the invention should in no way be construed as being limited to this example but rather should be construed to encompass any and all variations which become evident as a result of the teaching provided herein.

EXAMPLE

Figure 2:
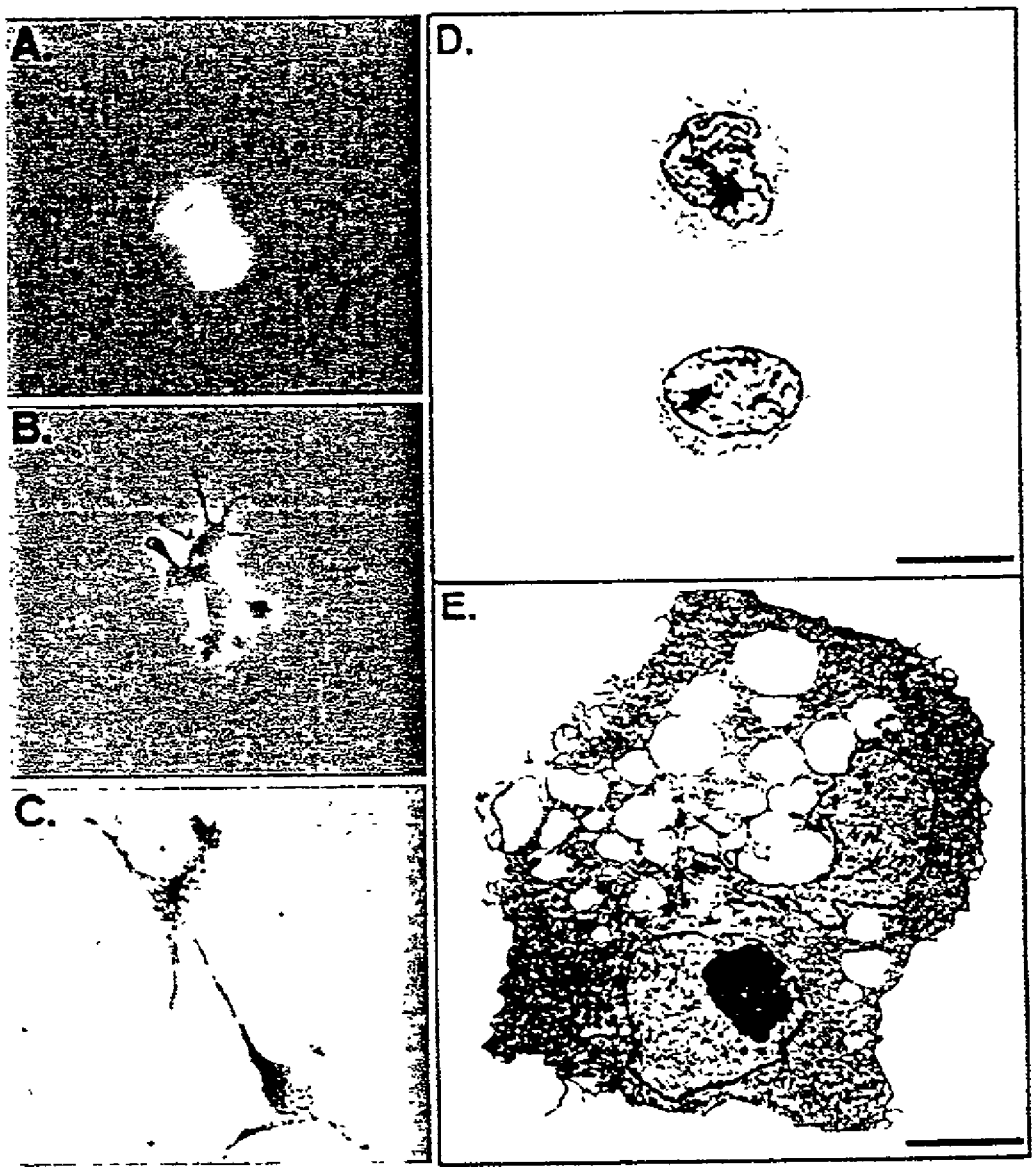
FIG. 2, comprising
Figure 3:
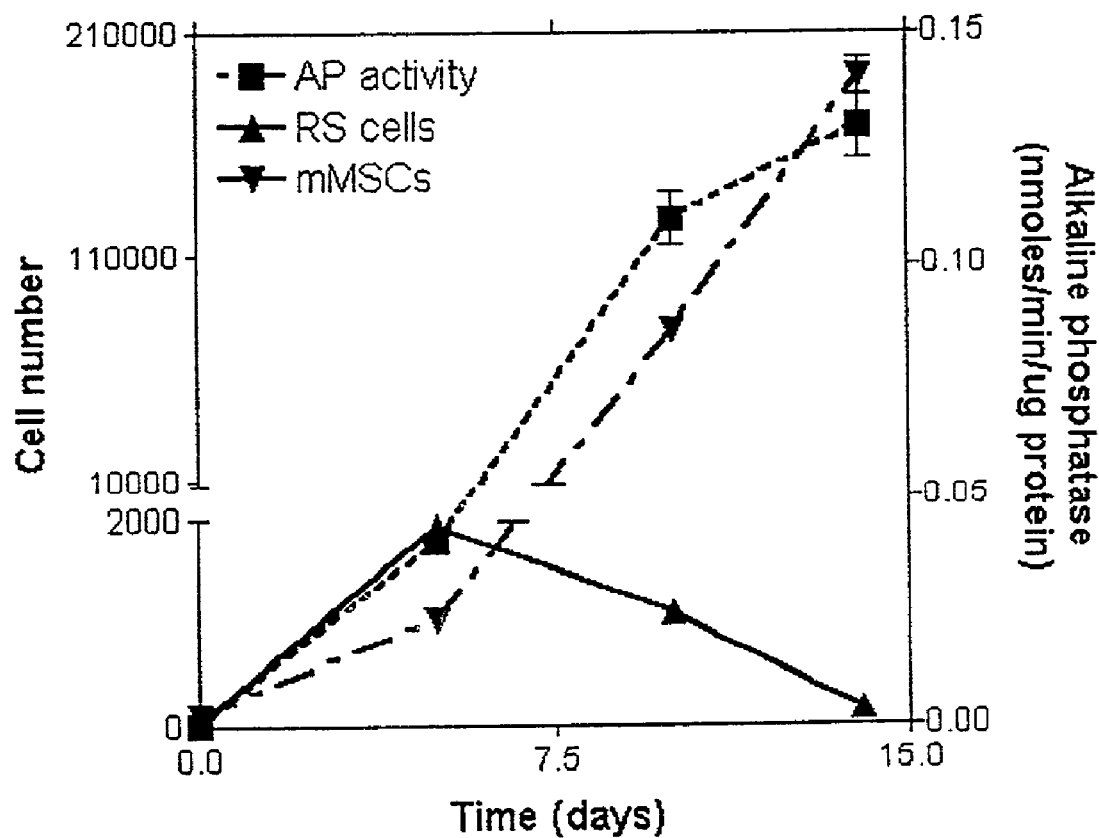
FIG. 3 is a graph depicting a time course for the expansion of cells and the alkaline phosphatase activity in cultures of MSCs. MSCs were plated at an initial density of about 3 cells/cm$^2$ in 75 cm$^2$ plates. Cell number was counted using a hemocytometer and the relative number of RS cells (RS-1 and RS-2) and mMSCs was assayed by FACS (25). Alkaline phosphatase activity was assayed in cell lysates with a p-nitrophenol phosphate disodium solution (Sigma 104).

To prepare cultures of human MSCs, nucleated cells were isolated from bone marrow aspirates from normal volunteers and the plastic adherent cells isolated (21, 25, 32). Thereafter, the cells were expanded by plating at an initial density of about 3 cells/cm$^2$ (25). The cultures underwent an initial lag phase of about five days during which the colonies were seen to arise from single cells. The colonies that were formed during the lag phase arose from either small round cells or small spindle-shaped cells. Large adherent cells in the cultures replicated slowly. After about five days, each of the colonies contained twenty to one hundred cells (FIGS. 1 and 2). The cells were widely separated in the colonies and were of two morphologically distinct types originally described by Mets and Verdonk (3): Small and rapidly self-replicating cells (RS cells) and large mature cells that divided slowly (mMSCs). In the 5-day cultures, RS cells accounted for over half of the cells (FIG. 3) and their rapid replication was apparent by time-lapse photography (FIGS. 2A, 2B and 2C). To prepare purified fractions of RS cells, cells from 14-day cultures were passed through a 10-micron filter (Millipore). The RS cells in the filtrate were about 7 microns in diameter and had a high nucleus to cytoplasm ratio (FIG. 2D). In contrast, mMSCs retained on the filter were 15 to 50 microns in diameter and contained a large number of unidentified vacuoles (FIG. 2E). During the logarithmic growth phase from about day 6 to day 12, the proportion of RS cells decreased and the proportion of mMSCs greatly increased (FIG. 3). The increase in mMSCs was accompanied by an increase in alkaline phosphatase (FIG. 3), an observation suggesting that some of the cells were differentiating into osteoblast precursors.

Figure 4:
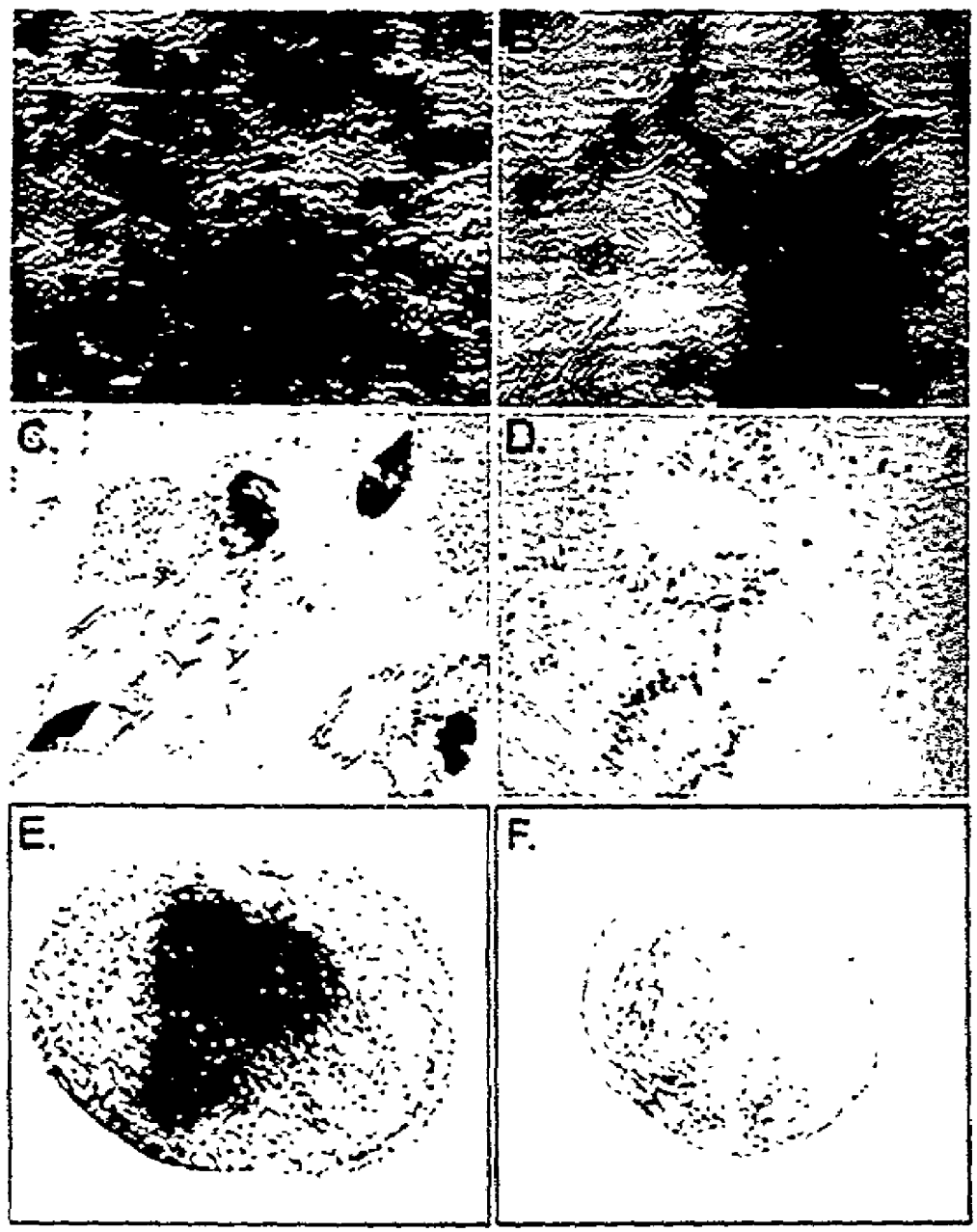
FIG. 4, comprising

The ultrafiltration procedure provided only a small yield of purified RS cells because the mMSCs rapidly obstructed the filter pores. Therefore, to test the multipotentiality for differentiation of the two types of cells, cultures that were incubated for 5 days and that contained about 60% RS cells were compared with cultures that were incubated for 12 days and that contained about 90% mMSCs (FIG. 3). After the cells were replated at about 5,000 cells per cm$^2$ and incubated in osteogenic medium for 21 days (33), the preparations enriched of RS cells more extensively differentiated into osteoblasts than the preparations enriched for mMSCs (FIGS. 4A and 4B). The area of mineralization (21) was 1.4 to 1.7 times greater with the RS cells. After incubation in adipogenic medium under similar conditions, the preparations enriched for RS cells differentiated more extensively into adipocytes than the preparations enriched for mMSCs (FIGS. 4C and 4D). The number of adipocytes was 3.5- to 6-fold greater with the RS cells. Also, after the cells were aggregated into micropellets and incubated in chondrogenic medium for 21 days (33), the cultures enriched for RS cells differentiated more extensively into cartilage (FIGS. 4E and 4F). The cartilage pellets obtained with the RS-enriched cultures were larger, and they more extensively stained for proteoglycans (FIGS. 4E and 4F). They also contained 1.6-fold higher levels of mRNA for type II collagen as assayed by RT-PCR.

To identify surface epitopes, cultures enriched for RS cells and mMSCs were assayed using a series of commercially available antibodies. As noted previously (25), FACS analyses distinguished two subtypes of RS cells: Small and agranular cells (RS-1 cells) seen in stationary and late-log phase cultures, and small granular cells (RS-2 cells) that were seen primarily at the end of the lag phase and that were probably mitotic RS-1 cells. The RS-1 cells and some of the RS-2 cells contained four epitopes not found on mMSCs (Table I): The VEGF receptor-2(FLK-1), TRK (an NFG receptor), transferrin receptor, and annexin II (lipocortin 2). Some but not all of the RS cells contained several other distinguishing epitopes. These epitopes included c-Kit (CD 117), the stem cell factor receptor. Also, some but not all the RS cells contained the epitope the multi-drug resistance gene that is a distinguishing feature of the "side population" of small cells from both muscle and marrow that are precursors of both hematopoietic and muscle cells (28, 29). However, all the cells in the culture were negative for the hematopoietic stem cell marker CD34 and a series of other markers for hematopoietic precursors. Also of interest was that both the RS-1 and RS-2 cells were negative for STRO-1, an epitope originally suggested as a marker for MSCs (30, 31). However, some of the mMSCs contained the STRO-1 epitope, an observation consistent with their ability to differentiate into osteoblasts (21). Some of the mMSCs contained several other epitopes not found on RS cells. These included receptors for PDGF and EGF, an observation suggesting that the previously reported stimulatory effects of these two cytokines in cultures of MSCs primarily expanded the subpopulation of mMSCs (11, 17).

To further characterize the subpopulations, proteins differentially expressed in preparations enriched for RS cells and mMSCs were assayed by preparing two-dimensional gels and identifying the proteins by mass spectrometry. Over 30 proteins were identified in fractions enriched for RS cells that were not detected in fractions enriched for mMSCs (Table II). Conversely, over 10 proteins were identified in fractions enriched for mMSCs that were not detected in fractions enriched for RS cells.

Although cultures of MSCs have been studied extensively for over 30 years (1), rigorous criteria for characterizing the cells have not been developed. Therefore, it is difficult to compare the data from different laboratories. The issue has become particularly pressing since several trials have been initiated in which cultures of MSCs are being used in patients (22, 24). Several groups of investigators developed protocols for preparation of human MSCs by using the criteria of morphologic homogeneity of the cultures and uniform staining with several antibodies (see ref. 18). Cultures of human MSCs become morphologically homogeneous only after they were passed several times at high density and lose some of their potential for multilineage differentiation (31). In contrast, early passage cells and cultures passaged at very low plating densities to generate single-cell derived colonies contained both the small cells and the large cells originally described by Mets and Verdonk (3). The fraction of small RS cells was directly proportional to the rate of proliferation and the ease with which the cells differentiated into multiple lineages in culture. Therefore, the results raise the possibility that RS cells are the most stem-cell like components of the cultures and may have the greatest potential for long-term engraftment and differentiation in vivo. As the results here emphasized however, even the sub-population defined as RS cells were heterogeneous since they did not stain uniformly for several surface epitopes. Therefore it will be of interest to further sub-fractionate the RS cell population and determine the potentials of the sub-populations for multilineage differentiation and for engraftment to specific tissues.

REFERENCES AND NOTES

1. A. J. Friedenstein, R. K. Chailakhjan, K. S. Lalykina, *Cell Tissue Kinet.* 3, 393–403 (1970).
2. H. Castro-Malaspina et al., *Blood* 56, 289–301 (1980).
3. T. S. Mets, G. Verdonk. *Mech. Ageing Dev.* 16, 81–89 (1981).
4. A. H. Piersma et al., *Exp. Hematol.* 13, 237–243 (1985).
5. M. E. Owen, A. J. Friedenstein, *Cell and Molecular Biology of Vertebrate Hard Tissues* (Ciba Foundation Symposium, Chichester, U.K., 1988), 42–60.
6. A. I. Caplan, *J. Orthoped. Res.* 9, 640–650 (1991).
7. B. R. Clark, A. Keating, *Ann. N. Y Acad. Sci.* 770, 70–78 (1995).
8. N. N. Beresford, J. H. Bennett, C. Devlin, P. S. Leboy, M. E. Owen, *J. Cell Sci.* 102, 341–351 (1992).
9. S. Wakitani, T. Saito, A. I. Caplan, *Muscle Nerve* 18, 1417–1426 (1995).
10. R. F. Pereira et al., *Proc. Natl. Acad. Sci. U.S.A.* 92, 4857–4861 (1995).
11. S. A. Kuznetsov, A. J. Friedenstein, P. G. Robey, *Br. J. Haematol.* 97, 561–570 (1997).
12. S. P. Bruder, N. Jaiswal, S. E. Haynesworth, *J. Cell Biochem.* 64, 287–294 (1997).
13. D. J. Prockop, *Science* 276, 71–74 (1997).
14. R. F. Pereira et al., *Proc. Natl. Acad. Sci. U.S.A.* 95, 7294–7299 (1998).
15. B. Johnstone et al., *Exp. Cell Res.* 238, 265–272 (1998).
16. G. Ferrari et al., *Science* 279, 1528–1530 (1998).
17. S. A. Azizi, D. G. Stokes, B. J. Augelli, C. M. DiGirolamo, D. J. Prockop, *Proc. Natl. Acad. Sci. U.S.A* 95, 3908–3913 (1998).
18. M. F. Pittenger et al., *Science* 284, 143–147 (1999).
19. S. K. Nilsson et al., *J Exp. Med.* 189, 729–734 (1999).
20. Z. Hou et al., *Proc. Natl. Acad. Sci.* 96, 7294–7299 (1999).
21. C. M. DiGirolamo et al., *Br. J. Haematol.* 107, 275–281 (1999).
22. E. M. Horwitz et al., *Nat. Med.* 5, 309–313 (1999).
23. G. C. Kopen, D. J. Prockop, D. G. Phinney, *Proc. Natl. Acad. Sci. U.S.A* 96, 10711–10716 (1999).
24. A. I. Caplan, *Clin. Orthoped.* 379, 567–570 (2000).
25. D. Colter, R. Class, C. M. DiGirolamo, D. J. Prockop, *Proc. Natl. Acad. Sci.* 97, 3213–3218 (2000).
26. M. Chopp et al., *Neuroreport* II, 3001–3005 (2000).
27. D. Woodbury, E. J. Schwarz, D. J. Prockop, *J. Neuroscience Res.* 61, 364–370 (2000).
28. M. A. Goodell et al., *Nat. Med.* 3, 1337–1345 (1997).
29. K. A. Jackson, T. Mi, M. A. Goodell, *Proc. Natl. Acad. Sci.* 96, 14482–14486 (1999).
30. S. Gronthos et al., *J. Bone Miner. Res.* 14, 47–56 (1999).
31. S. Walsh et al, *Bone* 27, 185–195 (2000).
32. To isolate human MSCs, 20 ml bone marrow aspirates were taken from the iliac crest of normal donors ranging in age from 19 to 49 years old under an IRB approved protocol. Nucleated cells were isolated with a density gradient (Ficoll-Paque) and resuspended in complete culture medium (α MEM, GIBCO BRL; 20% fetal bovine serum, lot-selected for rapid growth of MSCs, Atlanta Biologicals; 100 units/ml penicillin; 100 µg/ml streptomycin; and 2 mM L-glutamine, GIBCO BRL). All of the cells were plated in 25 ml medium in a 175 $cm^2$ culture dish (Falcon) and incubated at 37° C. with 5% humidified $CO_2$. After 24 h, non-adherent cells were discarded, and adherent cells were thoroughly washed twice with phosphate-buffered saline. The cells were incubated for 5 to 7 days, harvested with 0.25% trypsin and 1 mM EDTA for 5 min at 37° C., and then replated at about 3 cells/$cm^2$ in an intercommunicating system of culture flasks (6320 $cm^2$; Cell Factory; Nunc). After 14 days, the cells (from passage 1) were harvested with trypsin/EDTA, suspended at 1~2×10⁶ cells/ml in 5% DMSO and 30% fetal bovine serum, and frozen at 1 ml aliquots in liquid nitrogen. To expand a culture, a frozen stock of MSCs was thawed, plated at 5,000 cells/cm², and incubated for 5 to 7 days. The cells were harvested and diluted for further expanding by plating at initial densities of about 3 cells/cm². In colony-forming unit assays, cultures incubated for 10 to 14 days were washed with PBS and stained with 0.5% Crystal Violet in methanol for 5 to 10 min at room temperature.

33. For osteogenic differentiation, cells were plated at 1,000 cells per cm² in 2 cm² wells and grown to 50 to 70% confluency in 5 days. They were then incubated in osteogenic medium ($10^{-8}$M dexamethasone; 0.2 mM ascorbic acid, Sigma; and 10 mM β-glycerolphosphate, Sigma). The medium was replaced every 3 to 4 days for 21 days. Cultures were washed with PBS, fixed in a solution of ice-cold 70% ethanol for 1 h, and stained for 10 min with 1 ml of 40 mM Alizarin red (pH 4:1; Sigma) with rotation (21). For adipogenic differentiation, 50 to 70% confluent cultures were incubated in complete medium supplemented with 0.5 μM hydrocortisone, 0.5 mM isobutylmethylxanthine, and 60 μM indomethacin. The medium was replaced every 3 to 4 days for 21 days. Cells were washed with PBS, fixed in 10% formalin for 10 min, and stained for 15 min with fresh Oil Red-O solution (21). For chondrogenic differentiation, the pellet culture system of Johnstone, et al. (15) was modified. After 200,000 MSCs were centrifuged in 15 ml polypropylene tube, the pellets were cultured in chondrogenic media that consisted of high-glucose DMEM (Cellgro, Mediatech, Inc., Herndon, Va.) supplemented with 500 ng/ml BMP-6 (R&D systems, MN) as well as 10 ng/ml TGF-β3, $10^{-7}$M dexamethasone, 50 μg/ml ascorbate-2-phosphate, 40 μg/ml proline, 100 μg/ml pyruvate, 50 mg/ml ITS+™Premix (Becton Dickinson, MA: 6.25 μg/ml insulin, 6.25 μg/ml transferrin, 6.25 ng/ml selenious acid, 1.25 mg/ml bovine serum albumin, 5.35 mg/ml linoleic acid). The medium was replaced every 2 to 3 days for 21 days. The pellets were embedded in paraffin, cut in 5 mm sections, and stained with Safranin O.

34. For analysis of surface epitopes by FACS, the cells were suspended in PBS at a concentration of about 100,000 cells/ml. The cells were fixed in 1% methanol or acetone at 4° C. for 10 min and washed with PBS. Nonspecific antigens were blocked by incubating the cells at room temperature for 1 h in 1% BSA, 0.1% FCS, and 0.1% goat serum. The cells were washed by centrifugation in three volumes of PBS, and the cell pellet was suspended in 0.5 ml of a primary antibody solution containing 20 μg/ml of antibody, 1% BSA, and 0.1% goat serum. After incubation for 40 min at 4° C., the cells were washed in PBS. The primary antibodies were mouse or rabbit anti-human, obtained from Chemicon, IgM Hybridoma Bank, University of Iowa; PharMingen; Biomedia; and Santa Cruz Biotechnology. For an isotype control, nonspecific mouse or rabbit IgG (DAKO, Pharmingen, Chemicon, or Santa Cruz) was substituted for the primary antibody. For antibodies that required a second antibody for detection, the cell pellet was incubated under the same conditions for 20 min with antimouse or antirabbit IgG labeled with FITC or phycoerythrin. The cells were then washed in PBS and suspended in 1 ml of PBS for analysis on a cell sorter (FACsort; Becton Dickinson).

35. For protein analysis, cell pellets of about 3 million cells were vortexed in 1 ml of lysis buffer (3 mg/ml SDS, 30 mg/ml DTT in 30 mM Tris-HCl buffer, pH 7.8), and heated to 80 to 90° C. for 5 min. Ten μl of nuclease buffer containing 10U of DNase (Boehringer-Mannheim) and 10 μg of RNAse (Boehringer-Mannheim) was added and the sample was incubated at 37° C. for 5 to 10 min. The protein was precipitated with 5 ml acetone at 4° C., recovered by centrifugation, air dried and dissolved at a concentration of 10 mg/ml of solubilization buffer (2.1 g urea, 0.8 g thiourea, 200 mg CHAPS and 40 mg DTT in 5 ml water). The samples were separated first by isoelectric focusing (Immobilized pH Gradient Stripe, pH 3 to 10; Pharmacia) and then on 10 to 12% polyacrylamide gels in SDS. The gels were stained (Silver Plus, BioRad) and protein spots distinguishing RS cells from mMSCs were identified either by MOLDI-TOF before and after tryptic digestion or by LC/MS/MS.

36. Electron micrographs were prepared by the Biomedical Imaging Core Facility of the University of Pennsylvania Medical Center. The preparation of two-dimensional gels and analysis of proteins by mass spectrometry was performed for us by the W.M. Keck Biomedical Mass Spectrometry Laboratory, Biomedical Research Facility, University of Virginia, Charlottesville, Va.

TABLE I

Surface epitopes for RS cells and mMSCs

| Epitopes | RS-1 cells | RS-2 cells | mMSCs |
|---|---|---|---|
| Selective for RS cells | | | |
| VEGF receptor (FLK-1) | (+) | (+/−) | (−) |
| TRK (C-14; a NGF receptor) | (+) | (+/−) | (−) |
| Transferrin receptor | (+) | NA | (−) |
| Annexin II (Lipocortin 2) | (+) | NA | (−) |
| Multi-drug resistance | (+/−) | (+/−) | (−) |
| Epithelial membrane antigen | (+/−) | (+/−) | (−) |
| CD4 | (+/−) | (+/−) | (−) |
| CD104 | (+/−) | (+/−) | (−) |
| CD117 (c-Kit; stem cell factor receptor) | (+/−) | (+/−) | (−) |
| Selective for mMSCs | | | |
| STRO-1 | (−) | (−) | (+/−) |
| PDGF-R | (−) | (−) | (+/−) |
| EGF-R | (−) | (−) | (+/−) |
| CD10 | (−) | (−) | (+) |
| CD147 (Neuroregulin) | (−) | (−) | (+) |
| Non-selective | | | |
| Annexin V (Lipocortin 5) | (+/−) | NA | (+/−) |
| HLA-1 | (+/−) | (+/−) | (+/−) |
| Basic FGF receptor | (+/−) | (+/−) | (+/−) |
| CD31 | (+/−) | (+/−) | (+/−) |
| CD38 | (+/−) | (+/−) | (+/−) |
| CD44 (Hyaluronic acid receptor) | (+) | (−) | (+) |
| CD49e (integrin alpha 5) | (+) | (+) | (+) |
| CD59 | (+) | (−) | (+) |
| CD81 | (+/−) | (−) | (+) |
| CD90 (Thy-1) | (+/−) | (−) | (+) |

Symbols:
(+), most cells positive;
(+/−), some cells positive;
(−) negative.
All three subpopulations of MSCs are negative for: (a) Hematopoietic markers: CD1a, CD11B (Mac-1), CD14, CD27, CD34, CD43, CD45, CD133 and (b) other markers: CD50 (I-CAM 3), CD53, CD109, CD114 (G-CSFR), HLA-2, CCR5 (chemokine receptor-5), human L1 (neurite adhesion molecule).

TABLE II

Proteins differentially expressed in RS cells and mMSCs.

| Classification | RS cells | mMSCs |
|---|---|---|
| Stress proteins | Heat shock 27<br>Tumor rejection antigen (gp 96)<br>Glutathione-S transferase<br>Peroxiredoxin 1 | T-complex protein, 1-alpha |
| Ion channel and transport | Voltage-dependent-anion channel-2 | |
| Signal transduction | Protein kinase C substrate<br>Phosphatase 2A Inhibitor | |
| DNA synthesis/repair/Recombination | Esterase D<br>RNase A | |
| Protein synthesis | Initiation factor 5a<br>Elongation factor 1-alpha<br>Ribosomal protein S12<br>Ribosomal protein, large, P1<br>Ribosomal protein, large, P2 | Initiation factor 2G<br>Ribosomal protein, large, P0 |
| Transcription | Transcription factor BTF 3a | |
| Surface | Annexin I (lipocortin I)<br>Annexin II (lipocortin II) | Annexin V |
| Cytoskeleton | Destrin<br>Myosin light chain | Actin β chain |
| Metabolic | Lactate dehydrogenase A<br>Alpha-amylase inhibitor CM3<br>Dehydrogenase<br>Citrate synthetase<br>Transketolase<br>P-Glycerolmutase<br>Aldo-keto reductase 7(A2)<br>Enoyl-CoA hydratase<br>Proteosome subunit, alpha-4<br>Glycerolaldehyde-3-P | Lactate dehydrogenase B<br>Phosphoglycerate kinase-1<br>Enolase-1<br>Protein disulfide isomerase ER60 precursor |

What is claimed is:

1. A population of human marrow stromal cells enriched for small and rapidly self-renewing stem (RS) cells, said population comprising about 95% RS cells, wherein said RS cells are about seven microns in diameter, comprise granular and agranular cells, and do not express STRO-1, PDGF-R, EGF-R, CD10 and CD147.

2. The population of human marrow stromal cells of claim 1, wherein said population enriched for RS cells has an increased capacity for multilineage differentiation compared to a population of human marrow stromal cells not enriched for RS cells.

3. The population of human marrow stromal cells of claim 1, wherein said RS cells have a high nucleus to cytoplasm ratio.

4. The population of human marrow stromal cells of claim 1, further wherein said RS cells express at least one of the polypeptides selected from the group consisting of VEGF receptor-2 (FLK-1), TRK (an NGF receptor), transferrmn receptor, annexin II (lipocortin 2) and CD49e (integrin alpha 5).

5. The population of human marrow stromal cells of claim 1, further wherein cells within a first subtype of said RS cells are agranular and express VEGF receptor-2 (FLK-1), TRK (an NGF receptor), transferrin receptor, and annexin II.

6. The population of human marrow stromal cells of claim 5, further wherein said cells within a first subtype express CD44 (Hyaluronic acid receptor), CD49e (integrin alpha 5) and CD59.

7. The population of human marrow stromal cells of claim 1, further wherein cells within a second subtype of said RS cells are granular, express CD49e (integrin alpha 5) and do not express CD44 (Hyaluronic acid receptor) and CD59.

8. The population of human marrow stromal cells of claim 7, further wherein said cells within a second subtype do not express CD81 and CD90.

9. The population of human marrow stromal cells of claim 1, further wherein said RS cells express heat shock protein-27, tumor rejection antigen, glutathione-S transferase, peroxiredoxin 1, voltage-dependent-anion channel-2, protein kinase C substrate, phosphatase 2A inhibitor, esterase D, RNase A, initiation factor 5a, elongation factor 1-alpha, ribosomal protein S12, ribosomal protein large P1, ribosomal protein large P2, transcription factor BTF 3a, annexin I, destrin, myosin light chain, lactate dehydrogenase A, glycerolaldehyde-3-P dehydrogenase, citrate synthetase, transketolase, P-glycerolmutase, aldo-keto reductase 7(A2), alpha-amylase inhibitor CM3, enoyl-CoA hydratase, and proteosome subunit alpha-4.

* * * * *